United States Patent
Hunt (10) Patent No.: US 9,655,571 B2
(45) Date of Patent: May 23, 2017

(54) X-RAY SHIELD (71) Applicant: Kenex (Electro-Medical) Limited, Harlow Essex (GB)

(72) Inventor: Kenneth Hunt, Stansted Mountfitchet (GB)

(73) Assignee: Kenex (Electro-Medical) Limited, Harlow (GB)

( * ) Notice: Subject to any disclaimer, the term of this patent is extended or adjusted under 35 U.S.C. 154(b) by 0 days.

(21) Appl. No.: 14/913,921

(22) PCT Filed: Sep. 4, 2014

(86) PCT No.: PCT/GB2014/052682
§ 371 (c)(1),
(2) Date: Feb. 23, 2016

(87) PCT Pub. No.: WO2015/036736
PCT Pub. Date: Mar. 19, 2015

(65) Prior Publication Data
US 2016/0199011 A1 Jul. 14, 2016

(30) Foreign Application Priority Data
Sep. 10, 2013 (GB) .................................. 1316065.0

(51) Int. Cl.
*A61B 6/00* (2006.01)
*A61B 6/10* (2006.01)
*A61B 6/04* (2006.01)

(52) U.S. Cl.
CPC ............ *A61B 6/107* (2013.01); *A61B 6/0407* (2013.01); *A61B 6/102* (2013.01); *A61B 6/4435* (2013.01)

(58) Field of Classification Search
CPC ....... A61B 6/107; A61B 6/0407; A61B 6/102; A61B 6/4435
(Continued)

(56) References Cited

U.S. PATENT DOCUMENTS 5,006,718 A * 4/1991 Lenhart .................... G21F 3/00
250/515.1
5,600,702 A 2/1997 Pigg
(Continued)

FOREIGN PATENT DOCUMENTS

DE 3326880 A1 2/1985
EP 1613217 A1 1/2006
(Continued)

OTHER PUBLICATIONS

English abstract of European Patent No. EP 1613217 A1, European Patent Office, Jan. 11, 2006.
(Continued)

*Primary Examiner* — Michael Maskell
(74) *Attorney, Agent, or Firm* — DASCENZO Intellectual Property Law, P.C.

(57) ABSTRACT

An X-ray shield for a horizontal X-ray procedure table, the X-ray shield comprising a horizontal support bar comprising at least one substantially vertically aligned slot, in combination with an X-ray opaque top shield comprising at least one downwardly projecting pin, the at least one pin being arranged so as to be disposable within the at least one slot from above in order to engage the top shield with the horizontal support bar, the X-ray shield further comprising a latch engagable to prevent the separation of the top shield from the support bar when the top shield is engaged with the support bar, and wherein the latch can be unengaged to permit the removal of the top shield from the support bar by withdrawing the as least one pin from the at least one slot.

13 Claims, 6 Drawing Sheets (58) Field of Classification Search
USPC .................................................... 250/505.1
See application file for complete search history.

(56) References Cited

U.S. PATENT DOCUMENTS

| | | | |
|---|---|---|---|
| 5,981,964 A | 11/1999 | McAuley et al. | |
| 2008/0093568 A1* | 4/2008 | Fox ........................ | A61B 6/107 250/515.1 |
| 2011/0103555 A1* | 5/2011 | Hunt ...................... | A61B 6/107 378/203 |
| 2012/0241652 A1 | 9/2012 | Jeschke | |

FOREIGN PATENT DOCUMENTS

| | | |
|---|---|---|
| GB | 745087 | 2/1956 |
| GB | 2429237 A | 2/2007 |
| WO | WO 03/101527 A1 | 12/2003 |
| WO | WO 2006/080698 A1 | 8/2006 |
| WO | WO 2009/017872 A1 | 2/2009 |
| WO | WO 2010/001177 A1 | 1/2010 |
| WO | WO 2010/146109 A1 | 12/2010 |

OTHER PUBLICATIONS

English abstract of PCT Patent Application Publication No. WO 2010/146109 A1, European Patent Office, Dec. 23, 2010.
Search Report issued in connection with United Kingdom Patent Application No. GB 1316065.0, 1 page, United Kingdom Intellectual Property Office, Feb. 19, 2014.
English language machine translation of German Patent Publication No. DE 3326880 A1, European Patent Office, Feb. 7, 1985.
Search Report issued in connection with Singapore Patent Application No. 11201600911T, Intellectual Property Office of Singapore, Feb. 23, 2017.

* cited by examiner

FIG. 6B

X-RAY SHIELD

TECHNICAL FIELD

The invention relates to X-ray shields for attachment to X-ray procedure tables to protect a physician from unwanted radiation during a procedure.

BACKGROUND

During certain interventional proceedings, e.g. those involving the insertion of an intravascular catheter, patients are required to lay supine on an X-ray procedure table. The physician then inserts an intravascular catheter through a small incision made in the patient's arm or groin, which is then guided to the desired location.

To facilitate this process the tip of the catheter is X-ray opaque, allowing the physician to guide the catheter under fluoroscopic observation.

Fluoroscopic observation is a real-time imaging technique involving placing the patient between an X-ray emitting tube and an image intensifier or digital detector. Typically the X-ray tube is carried by the lower end of a C-shaped arm with the detector positioned at the other end. Such C-arms are freely moveable to permit a wide range of radiographic views of the patient.

During a procedure the physician passes the catheter through the patient and tracks its location on a monitor, which gives a visual representation of the radiation received by the digital detector. Typically the X-ray tube is located underneath the table and the physician moves the C-arm accordingly to continue tracking the location of the catheter as the procedure continues.

Although the majority of the X-rays pass through the table, to the patient and to the detector, inevitably there is some scatter. As such interventional procedures often take an extended time to complete, this has the potential to expose the physician to a significant amount of radiation.

To reduce exposure to radiation, a number of X-ray protection table mounted shields have been developed, for example those shown in U.S. Pat. No. 5,006,718 and U.S. Pat. No. 5,981,964, which involve a flexible X-ray curtain positioned between the physician and patient and extending from the side of the table to the floor. Such shields have a horizontal hinge to allow the shield to be repositioned to allow for the passage of a C-arm during a procedure.

However, inevitably there will be occasions where, for whatever reason, the shield is not repositioned during movement of the C-arm, resulting in a collision between the C-arm and shield. For example, the position of the shield may not be apparent if it is covered with sterile drapes, as often happens. Additionally the physician will be concentrating on the procedure at hand and may not realise that movement of the C-arm may result in a collision.

Such C-arms are often fitted with collision detection devices for safety reasons, however even though this may reduce the risk of damage to equipment, the procedure will be interrupted and may result in its cancellation.

WO 2010/001177 A1 discloses an improved table-mounted X-ray shield for a horizontal X-ray procedure table, comprising a horizontal support bar for attachment to a first depending X-ray opaque curtain and a second support bar, the second support bar being moveably attached to the horizontal support bar to enable movement of the second support bar in both horizontal and vertical directions.

Such X-ray shields may also comprise a so-called top shield, which extends above such a horizontal support bar, rather than depending from it.

An important technical feature of such top shields is that they can be quickly positioned and are readily removable during a procedure by a physician or an assistant. In one common design such top shields are attached to the horizontal support bar by locating pins which pass through vertical channels in the horizontal support bar. As such top shields are typically fairly heavy due to the fact they are usually lead-lined, their weight alone keeps them in place with respect to the horizontal support arm.

However, in the event that a C-arm collides with the underside of such a horizontal support bar, the C-arm can push the top shield upwards and dislodge the guiding pins resulting in the top shield coming loose from the horizontal support arm. This could have the effect of the procedure being interrupted and may result in its cancellation.

Thus improvements in this area remain desirable.

SUMMARY OF THE INVENTION

The invention relates to an X-ray shield for a horizontal X-ray procedure table, the X-ray shield comprising a horizontal support bar comprising at least one substantially vertically aligned slot, in combination with an X-ray opaque top shield comprising at least one downwardly projecting pin, the at least one pin being arranged so as to be disposable within the at least one slot from above in order to engage the top shield with the horizontal support bar, the X-ray shield further comprising a latch engagable to prevent the separation of the top shield from the support bar when the top shield is engaged with the support bar, and wherein the latch can be unengaged to permit the removal of the top shield from the support bar by withdrawing the at least one pin from the at least one slot.

Thus, if a C-arm inadvertently collides with the X-ray shield from below, the top shield is prevented from disengaging from the support by the action of the latch. However when it is desired to remove the top shield from the support bar, the latch can be easily disengaged, permitting the immediate removal of the top shield from the support bar.

The top shield is typically rigid or semi-flexible and is a planar shield projecting substantially upwards from the horizontal support bar. Semi-flexible top shields are in common use and can be pushed over to some degree to cause them to bend to cover the patient.

Such semi-flexible top shields include flexible radiation attenuation materials, such as lead rubber or lead vinyl. During the manufacturing process lead powder is evenly dispersed throughout these materials. However lead-free materials are also available. Such flexible material is typically combined with a thin plastic sheet of polycarbonate or polypropylene.

In a preferred embodiment the top shield has two pins and the support bar has two corresponding slots for the pins to engage. This provides accurate positioning without an excessive number of pins.

In a preferred embodiment the latch is arranged so that it does not prevent the engagement of the top shield with the support bar, but once the top shield is engaged to the support bar, the latch acts to prevent their disengagement.

For example this can be achieved if the latch depends from the top shield and is bevelled so that it is pushed aside as the top shield engages with the support bar. Once the top shield is fully engaged with the support bar, the latch can then lock into place, e.g., by the action of gravity. Thus, no additional consideration need be given by the operator when installing the top shield.

When it is desired to remove the top shield then it is necessary to include the additional step of removing the latch to enable their disengagement. This step is essential to preventing the unintended disengagement of the top shield from the support bar during use.

In a preferred embodiment, the horizontal support bar is made up of a first horizontal support bar for attachment to a first depending X-ray opaque curtain and a second horizontal support bar, the second support bar being moveably attached to the horizontal support bar. In this embodiment it is preferable that the top shield is engagable with the second support bar as this allows the top shield to be moved aside together with the second support bar, in the event of a collision with a C-arm.

In a further preferred embodiment the second support bar is movably attached to the first support bar to enable movement of the second support bar in both horizontal and vertical directions.

Typically a depending X-ray opaque curtain is attached to the second support bar. This may be a continuation of the first depending curtain or could be a separate curtain. Such curtains are typically flexible and drapable. Additional X-ray curtains may be attached to the support bar, e.g. extending upwards from the bar. Such upwardly extending curtains may be rigid or semi-flexible in construction.

Typically the horizontal support bar is for attachment to a horizontal accessory rail on the side of a typical X-ray procedure table. The shield can therefore be fitted to existing tables to improve their performance without requiring a replacement table. Typically the X-ray opaque curtain or curtains are attached to the shield to form a complete unit for attachment to a table in the above manner.

Such X-ray procedure tables often do not have a constant width along their whole length and typically become narrower near the head of the table with the width contracting in sudden steps. In order for the shield to remain in close contact with the side of such a table, the horizontal support bar may be horizontally moveable, e.g. by comprising a hinge for horizontal movement of two rigid horizontal bar portions. This allows it to follow snugly any sudden contractions of the width of the table.

Preferably the second support bar is hingedly attached to the horizontal support bar, e.g. by a single multi-directional hinge or by a vertical hinge and a separate horizontal hinge. Preferably a vertical hinge and a separate horizontal hinge are used which may be together in a single unit or separated by a short connecting portion.

In a preferred embodiment, the second support bar is biased to return to a horizontal orientation under gravity. This enables the shield to take a horizontal orientation along its length under normal conditions. After a C-arm inadvertently collides with the second support bar it pushes the second support bar upwards and possibly also to the side. After the situation has been remedied the second support bar returns to horizontal under its own weight.

Preferably the shield is adapted so that it can be fitted to either side of an X-ray procedure table. This may, for example, be achievable by rotating the shield through 180°, maintaining the second attachment bar at the head end of the X-ray procedure table.

If this feature is to be combined with that of the second support bar being arranged to return to a horizontal orientation under gravity, then special considerations must be made for this. For example, the vertical hinge may be adaptable to permit movement away from horizontal in only one chosen direction, according to the position of a stopping pin in the hinge, which the user can position as desired.

BRIEF DESCRIPTION OF THE DRAWINGS

The invention will now be described, by way of illustration, with reference to the following figures, in which:—

DETAILED DESCRIPTION

Figure 1:
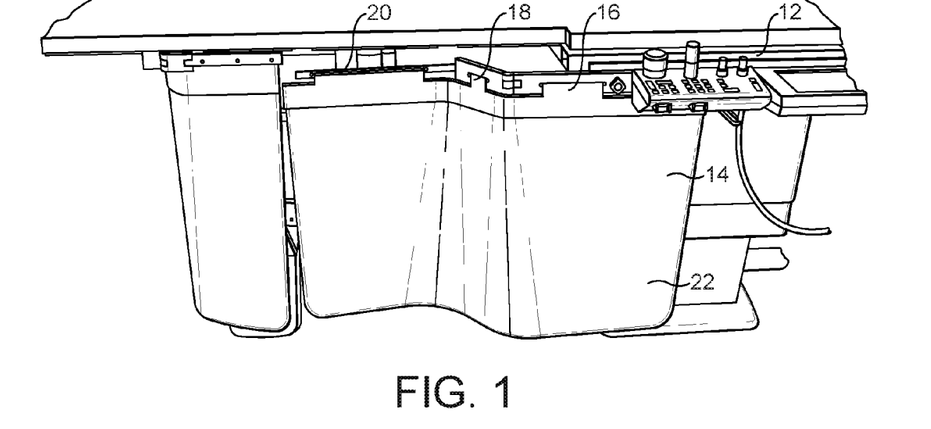
FIG. 1 is an image of an X-ray procedure table with a known X-ray shield attached.

Turning to the figures, FIG. 1 shows an X-ray procedure table 10 comprising a horizontal accessory rail 12 which has attached to it a known design of X-ray shield 14. The shield 14 can be seen to be made up of three horizontally hinged together support arms 16, 18, 20. Depending from the support arms is an X-ray opaque curtain 22.

Figure 2:
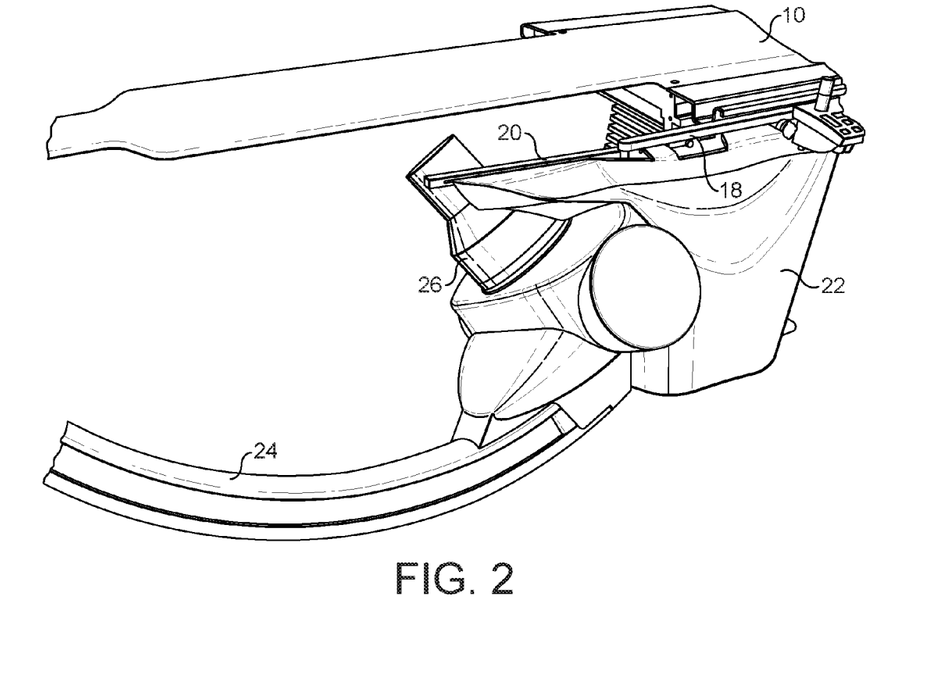
FIG. 2 is an image of the prior art arrangement as shown in FIG. 1 with a C-arm colliding with the shield.

FIG. 2 shows the arrangement as shown in FIG. 1 but where a C-arm 24 having at one end an X-ray emitter 26 is in collision with the horizontally hinged support arm 20. In this case either the C-arm will stop moving due to it possessing a collision detection device or the shield will be damaged. In either event the procedure will at least be interrupted and may need to be cancelled.

Figure 3:
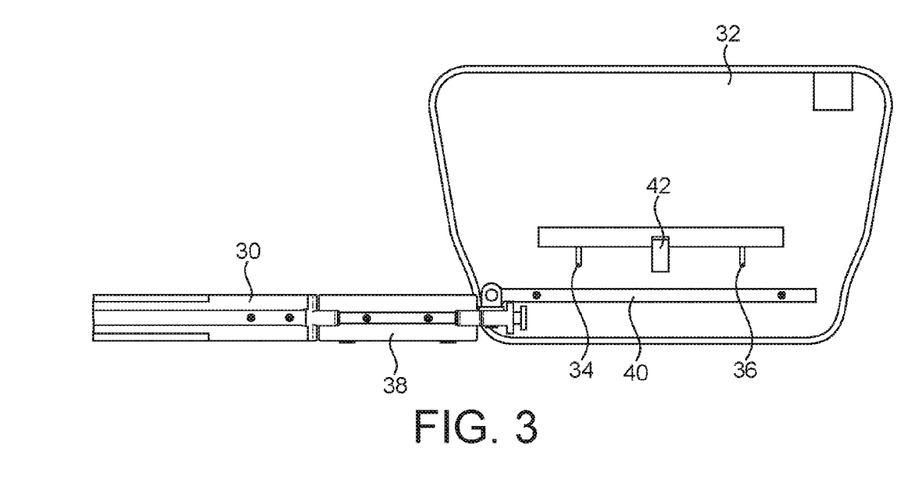
FIG. 3 is a side view of part of a horizontal support bar with a top shield in a disengaged position.
Figure 4:
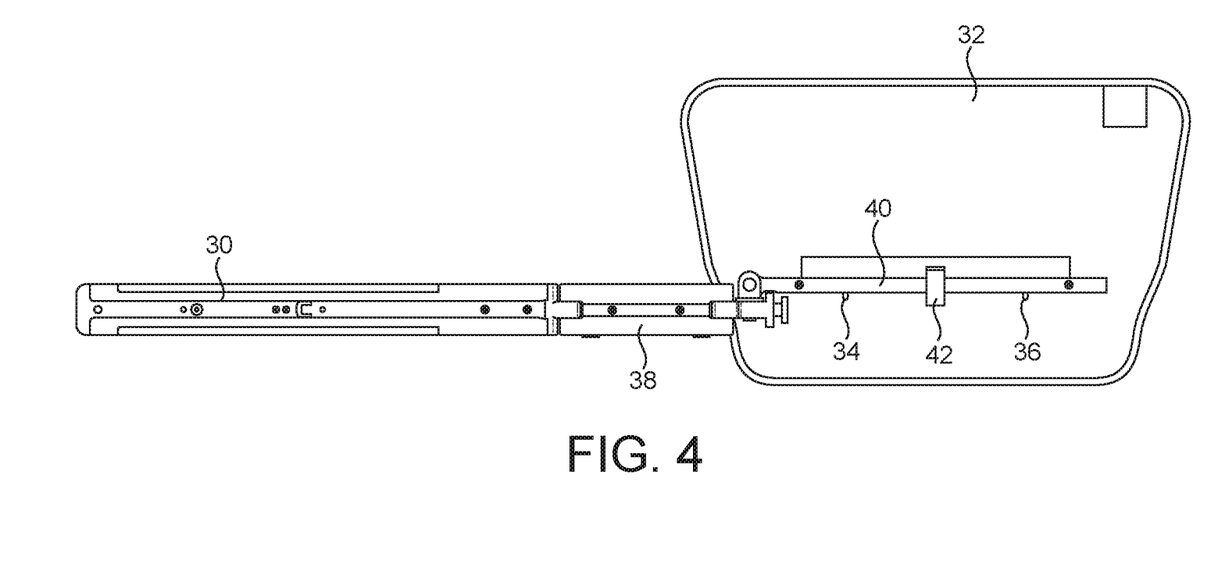
FIG. 4 is a side view of part of a horizontal support bar with a top shield in an engaged position.

FIGS. 3 and 4 show a horizontal support bar 30 and an associated X-ray top shield 32. The horizontal support bar 30 is made up of a first horizontal support bar 38 and a second horizontal support bar 40. The top shield 32 is semi-flexible and contains lead rubber with a thin plastic sheet of polycarbonate.

The top shield has two pins 34, 36 which, in use, are guided into respective slots (not visible) in the second support bar 40. The top shield also comprises a latch 42 which, in use, acts to lock the top shield 32 and the second horizontal support bar 40 together once engaged as shown in FIG. 4.

FIGS. 5A to 5D show sequentially the top shield 32 coming into engagement with the horizontal support bar 30 and engaging with the second horizontal support bar 40.

Figure 5A:
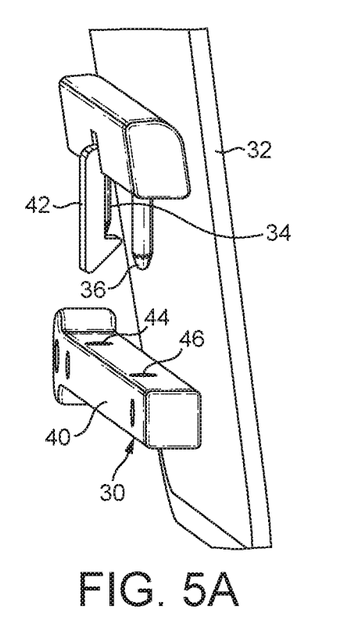
FIGS. 5A to 5D are side views of part of a horizontal support bar with a top shield showing various stages of engagement.

In FIG. 5A the top shield 32 can be seen with pin 36 and latch 42 depending from it. The latch 42 is bevelled on its lowermost end and depends freely under the action of gravity from the top shield 32.

Also shown are slots 44, 46 which are for receiving pins 34, 36 respectively.

Figure 5B:
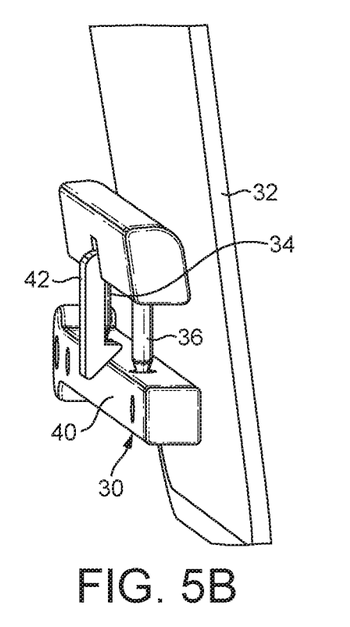
Figure 5C:
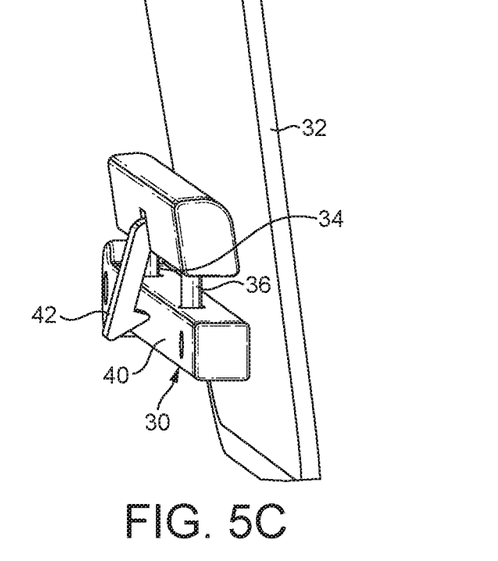

As shown in FIG. 5B the bevelled end of latch 42 is just in contact with second support bar 40. As the top shield moves closer to engage, as shown in FIG. 5C the latch 42 is deflected away due to the action of the bevelled edge on the horizontal support bar 40.

Figure 5D:
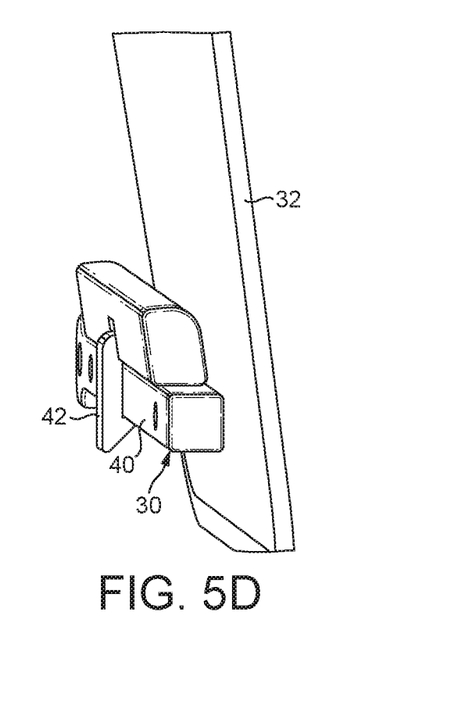

Once the top shield 32 is fully engaged with the second support bar 40, the latch 42 moves to a locking position as shown in FIG. 5D by the action of gravity. In this position the top shield 32 is locked in place to the second support bar 40 and cannot be easily dislodged without first activating the latch to an open position.

Figure 6A:
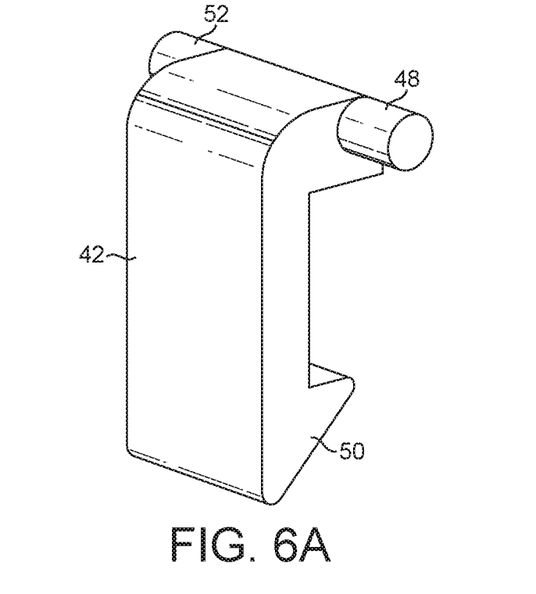
FIGS. 6A to 6B are perspective views of a latch for use in the present invention.
Figure 6B:
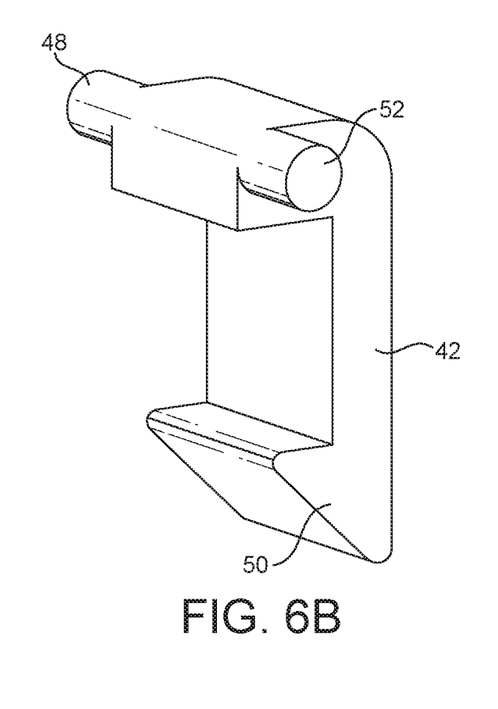

FIGS. 6A and 6B show two perspective views of latch 42. As can be seen latch 42 has two engaging bars 52, 48, which engage with the top shield 32 to allow the latch to be rotatably moveable relative thereto.

Also clearly shown is the bevelled end 50, which allows the top shield to engage with the support bar 40 automatically as discussed above.

The invention claimed is:

1. An X-ray shield for a horizontal X-ray procedure table, the X-ray shield comprising:
    a first horizontal support bar;
    a first depending X-ray opaque curtain attached to and depending downward from the first horizontal support bar;
    a second horizontal support bar comprising at least one substantially vertically aligned slot, the second support bar being movably attached to the first horizontal support bar; and
    an X-ray opaque top shield projecting substantially upwards from the second horizontal support bar and comprising at least one downwardly projecting pin, the at least one downwardly projecting pin being arranged so as to be disposable within the at least one substantially vertically aligned slot from above in order to engage the top shield with the second horizontal support bar, the top shield further comprising a latch engagable to prevent the separation of the top shield from the second horizontal support bar when the top shield is engaged with the second horizontal support bar, and wherein the latch can be unengaged to permit the removal of the top shield from the second horizontal support bar by withdrawing the at least one downwardly projecting pin from the at least one substantially vertically aligned slot.

2. The X-ray shield according to claim 1, wherein the top shield comprises a semi-flexible and planar shield.

3. The X-ray shield according to claim 1, wherein the at least one downwardly projecting pin comprises two downwardly projecting pins, and wherein the at least one substantially vertically aligned slot comprises two substantially vertically aligned slots corresponding to the two downwardly projecting pins.

4. The X-ray shield according to claim 1, wherein the latch is arranged so that it does not prevent the engagement of the top shield with the second horizontal support bar, but once the top shield is engaged to the second horizontal support bar, the latch acts to prevent their disengagement.

5. The X-ray shield according to claim 4, wherein the latch depends downward, is pivotally coupled relative to the at least one downwardly projecting pin, and is bevelled so that it is pushed aside as the top shield engages with the second horizontal support bar, and once the top shield is fully engaged with the second horizontal support bar, the latch can then lock into place by the action of gravity.

6. The X-ray shield according to claim 1, wherein the second horizontal support bar is movably attached to the first horizontal support bar to enable movement of the second horizontal support bar in both horizontal and vertical directions.

7. The X-ray shield according to claim 1, which is adapted for attachment to a horizontal accessory rail of the procedure table.

8. The X-ray shield according to claim 1, wherein the first and second horizontal support bars are horizontally moveable.

9. The X-ray shield according to claim 8, wherein the second horizontal support bar is hinged to the first horizontal support bar.

10. The X-ray shield according to claim 1, wherein the second horizontal support bar is biased to return to a horizontal orientation under gravity.

11. The X-ray shield according to claim 1, which is adapted so that it can be fitted to either side of the X-ray procedure table.

12. The X-ray shield according to claim 1,
    wherein the top shield comprises:
        a semi-flexible and planar shield; and
        a housing secured to the semi-flexible and planar shield;
    wherein the at least one downwardly projecting pin comprises two spaced-apart pins that project downward from the housing;
    wherein the at least one substantially vertically aligned slot comprises two substantially vertically aligned slots corresponding to the two downwardly projecting pins;
    wherein the latch is pivotally coupled to the housing and projects downward from the housing between the two spaced-apart pins;
    wherein the latch is configured to pivot away from the semi-flexible and planar shield when the latch engages the second horizontal support bar and when the housing is moved toward the second horizontal support bar from above the second horizontal support bar; and
    wherein the latch is configured to pivot toward the semi-flexible and planar shield by the action of gravity when the housing is moved into engagement with the second horizontal support bar from above the second horizontal support bar to lock the top shield into place with the second horizontal support bar.

13. An X-ray shield for a horizontal X-ray procedure table, the X-ray shield comprising:
    a horizontal support bar comprising two spaced-apart substantially vertically aligned slots;
    an X-ray opaque top shield projecting substantially upwards from the horizontal support bar and comprising:
        a semi-flexible and planar shield;
        a housing secured to the semi-flexible and planar shield;
        two spaced-apart pins projecting downward from the housing and arranged so as to be disposable within the two spaced-apart substantially vertically aligned slots from above in order to engage the top shield with the horizontal support bar; and
        a latch pivotally coupled to the housing and projecting downward from the housing between the two spaced-apart pins, wherein the latch is configured to pivot away from the semi-flexible and planar shield when the latch engages the horizontal support bar as the housing is moved toward the horizontal support bar from above the horizontal support bar, and wherein the latch is configured to pivot toward the semi-flexible and planar shield by the action of gravity when the housing is moved into engagement with the horizontal support bar from above the horizontal support bar to lock the top shield into place with the horizontal support bar.

* * * * *